United States Patent
Andree et al.

(10) Patent No.: US 6,815,398 B1
(45) Date of Patent: Nov. 9, 2004

(54) SUBSTITUTED PHENYLURACILS AND THEIR USE AS HERBICIDES

(75) Inventors: Roland Andree, Langenfeld (DE); Hans-Georg Schwarz, Langenfeld (DE); Mark Wilhelm Drewes, Langenfeld (DE); Dieter Feucht, Monheim (DE); Rolf Pontzen, Leichlingen (DE); Ingo Wetcholowsky, Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/129,632

(22) PCT Filed: Oct. 31, 2000

(86) PCT No.: PCT/EP00/10768

§ 371 (c)(1),
(2), (4) Date: May 7, 2002

(87) PCT Pub. No.: WO01/34575

PCT Pub. Date: May 17, 2001

(30) Foreign Application Priority Data

Nov. 11, 1999 (DE) .......................................... 199 54 312

(51) Int. Cl.⁷ ....................... C07D 239/54; A01N 43/54
(52) U.S. Cl. ....................................... 504/243; 544/312
(58) Field of Search ........................... 544/312; 504/243

(56) References Cited

U.S. PATENT DOCUMENTS

| | | | |
|---|---|---|---|
| 4,812,164 A | 3/1989 | Wenger et al. | 71/92 |
| 4,859,229 A | 8/1989 | Wenger et al. | 71/92 |
| 4,979,982 A | 12/1990 | Brouwer et al. | 71/92 |
| 5,084,084 A | 1/1992 | Satow et al. | 71/92 |
| 5,116,404 A | 5/1992 | Ishii et al. | 71/92 |
| 5,127,935 A | 7/1992 | Satow et al. | 71/92 |
| 5,134,144 A | 7/1992 | Brouwer et al. | 514/274 |
| 5,154,755 A | 10/1992 | Satow et al. | 71/92 |
| 5,169,430 A | 12/1992 | Strunk et al. | 71/92 |
| 5,183,492 A | 2/1993 | Suchy et al. | 504/243 |
| 5,266,554 A | 11/1993 | Suchy et al. | 504/243 |
| 5,280,010 A | 1/1994 | Enomoto et al. | 504/243 |
| 5,356,863 A | 10/1994 | Satow et al. | 504/243 |
| 5,486,610 A | 1/1996 | Strunk et al. | 544/311 |
| 5,593,945 A | 1/1997 | Andree et al. | 504/243 |
| 5,602,077 A | 2/1997 | Amuti et al. | 504/243 |
| 5,681,794 A | 10/1997 | Andree et al. | 504/243 |
| 6,110,870 A | 8/2000 | Andree et al. | 504/243 |

FOREIGN PATENT DOCUMENTS

| | | |
|---|---|---|
| DE | 195 04 229 | 8/1996 |
| EP | 0 597 360 | 5/1994 |
| WO | 97/01541 | 1/1997 |
| WO | 97/05116 | 2/1997 |
| WO | 98/41093 | 9/1998 |
| WO | 99/38851 | 8/1999 |
| WO | 00/02866 | 1/2000 |

OTHER PUBLICATIONS

J. Heterocycl. Chem., 9, (month unavailable) 1972m pp. 513–522, "Novel 6–(Trifluoromethyl)cytosines and 6–(Trifluoromethyl)uracils" by A. W. Lutz and S. H. Trotto.

*Primary Examiner*—Richard L. Raymond
(74) *Attorney, Agent, or Firm*—Richard E.L. Henderson; Raymond J. Harmuth

(57) ABSTRACT

Novel substituted phenyluracils of the general formula (I)

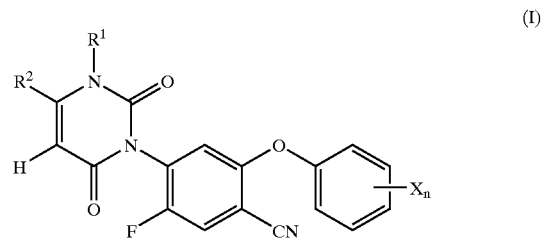

in which n represents 0, 1 or 2, $R^1$ represents hydrogen, amino or optionally substituted alkyl, $R^2$ represents carboxyl, cyano, carbamoyl, thiocarbamoyl or in each case optionally substituted alkyl or alkoxycarbonyl, X represents hydroxyl, mercapto, amino, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, phenylcarbonyloxy, alkylcarbonylamino, alkoxycarbonylamino, alkylsulphonylamino, alkenyl, alkenyloxy, alkenyloxycarbonyl, alkinyl, alkinyloxy or alkinyloxycarbonyl, where in the case that n is greater than 1, X in the individual possible compounds may also have meanings other than those given.

30 Claims, No Drawings

SUBSTITUTED PHENYLURACILS AND THEIR USE AS HERBICIDES

The present invention is the national stage of PCT/EP00/10768 filed Oct. 31, 2000, which in turn claims priority of German Patent DE 199 54 312.7 filed Nov. 11, 1999.

The invention relates to novel substituted phenyluracils and novel intermediates for their preparation and to their use as herbicides.

Certain substituted aryluracils are already known from the (patent) literature (cf. EP-A-255047, EP-A-260621, EP-A-408382, EP-A-438209, EP-A-473551, EP-A-517181, EP-A-563384, WO-A-91/00278, WO-A-91/07393, WO-A-93/14073, WO-A-98/41093, U.S. Pat. No. 4,979,982, U.S. Pat. No. 5,084,084, U.S. Pat. No. 5,127,935, U.S. Pat. No. 5,154,755, U.S. Pat. No. 5,169,430, U.S. Pat. No. 5,486,610, U.S. Pat. No. 5,356,863). However, these compounds have hitherto not attained any particular importance.

This invention, accordingly, provides novel substituted phenyluracils of the general formula (I)

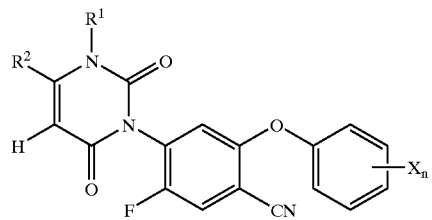

(I)

in which n represents the numbers 0, 1 or 2, $R^1$ represents hydrogen, amino or optionally substituted alkyl, $R^2$ represents carboxyl, cyano, carbamoyl, thiocarbamoyl or in each case optionally substituted alkyl or alkoxycarbonyl, X represents hydroxyl, mercapto, amino, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino, alkylcarbonyl, alkoxycarbonyl, alkylaminocarbonyl, dialkylaminocarbonyl, alkylcarbonyloxy, alkoxycarbonyloxy, alkylaminocarbonyloxy, dialkylaminocarbonyloxy, phenylcarbonyloxy, alkylcarbonylamino, alkoxycarbonylamino, alkylsulphonylamino, alkenyl, alkenyloxy, alkenyloxycarbonyl, alkinyl, alkinyloxy or alkinyloxycarbonyl—where in the case that n is greater than 1, X in the individual possible compounds may also have meanings other than those given.

In the definitions, the hydrocarbon chains, such as alkyl, are in each case straight-chain or branched—including in combination with heteroatoms, such as in alkoxy.

If the compounds of the general formula (I) according to the invention contain substituents with asymmetric carbon atoms, the invention relates in each case to the R enantiomers and the S enantiomers, and to any mixtures of these enantiomers, in particular the racemates.

n preferably represents the numbers 1 or 2.

$R^1$ preferably represents hydrogen, amino or optionally cyano-, carboxyl-, fluorine-, chlorine-, $C_1$–$C_4$-alkoxy- or $C_1$–$C_4$-alkoxy-carbonyl-substituted $C_1$–$C_4$-alkyl.

$R^2$ preferably represents carboxyl, cyano, carbamoyl, thiocarbamoyl or in each case optionally fluorine-substituted $C_1$–$C_4$-alkyl or $C_1$–$C_4$-alkoxy-carbonyl.

X preferably represents hydroxyl, mercapto, amino, nitro, cyano, carboxyl, carbamoyl, thiocarbamoyl, fluorine, chlorine, bromine, iodine, represents in each case optionally hydroxyl-, cyano-, carboxyl-, carbamoyl-, fluorine-, chlorine-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl-, $C_2$–$C_4$-alkenyl-oxycarbonyl-, $C_2$–$C_4$-alkinyl-oxycarbonyl-, $C_1$–$C_4$-alkylamino-carbonyl-, di-($C_1$–$C_4$-alkyl)-amino-carbonyl-, phenoxycarbonyl-, benzyloxy-carbonyl-, phenylaminocarbonyl-substituted alkyl, alkoxy, alkylthio, alkylsulphinyl, alkylsulphonyl or alkylamino having in each case 1 to 6 carbon atoms, represents dialkylamino having in each case 1 to 6 carbon atoms in the alkyl groups, represents in each case optionally cyano-, fluorine-, chlorine-, bromine- or $C_1$–$C_4$-alkoxy-substituted alkylcarbonyl, alkoxycarbonyl, alkylaminocarbonyl, alkylcarbonyloxy, alkoxycarbonyloxy or alkylaminocarbonyloxy having in each case 1 to 6 carbon atoms in the alkyl groups, represents dialkylaminocarbonyl or dialkylaminocarbonyloxy having in each case 1 to 6 carbon atoms in the alkyl groups, represents phenylcarbonyloxy, represents in each case optionally fluorine-, chlorine- or bromine-substituted alkylcarbonylamino, alkoxycarbonylamino, alkylsulphonylamino having in each case up to 6 carbon atoms, or represents in each case optionally cyano-, carboxyl-, fluorine-, chlorine-, bromine- or $C_1$–$C_4$-alkoxy-carbonyl-substituted alkenyl, alkenyloxy, alkenyloxycarbonyl, alkinyl, alkinyloxy or alkinyloxycarbonyl having in each case up to 6 carbon atoms.

n particularly preferably represents the number 1.

$R^1$ particularly preferably represents hydrogen, amino or methyl.

$R^2$ particularly preferably represents carboxyl, cyano, carbamoyl, methoxycarbonyl or trifluoromethyl.

X particularly preferably represents hydroxyl, mercapto, amino, nitro, cyano, carboxyl, carbamoyl, thiocarbamoyl, fluorine, chlorine, bromine, methyl, represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, allyloxycarbonyl-, 1-buten-3-yloxycarbonyl-, 2-buten-4-yl-oxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, methylsulphonyl, ethylsulphonyl, methylamino, ethylamino, n- or i-propylamino, n-, i-, s- or t-butylamino, represents dimethylamino or diethylamino, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, n- or i-butylaminocarbonyloxy, represents dimethylaminocarbonyl, diethylaminocarbonyl, dimethylaminocarbonyloxy or diethylaminocarbonyloxy, represents n- or i-butylcarbonyloxy, represents phenylcarbonyloxy, represents in each case optionally fluorine- or chlorine-substituted acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, or represents in each case optionally cyano-, carboxyl-, fluorine-, chlorine-, methoxycarbonyl- or ethoxycarbonyl-substituted ethenyl, propenyl, propenyloxy, propenyloxycarbonyl, ethinyl, propinyl, propinyloxy or propinyloxycarbonyl.

X very particularly preferably represents hydroxyl, mercapto, amino, represents in each case cyano-, carboxyl-, carbamoyl-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, allyloxycarbonyl-, 1-buten-3-yloxycarbonyl-, 2-buten-4-yloxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl- substituted methyl, methoxy, ethyl, n- or i-propyl, n-, i-, s- or t-butyl, ethoxy, n- or i-propoxy, methylthio, ethylthio, methylsulphinyl, ethylsulphinyl, methylsulphonyl or ethylsulphonyl, represents in each case cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, allyloxycarbonyl-, 1-buten-3-yloxycarbonyl-, 2-buten-4-yl-oxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted n-, i-, s- or t-butoxy, n- or i-propylthio, methylamino, ethylamino, n- or i-propylamino, n-, i-, s- or t-butylamino, represents dimethylamino or diethylamino, represents in each case cyano-, fluorine-, chlorine-, methoxy-, ethoxy-, n- or i-propoxy-substituted methoxycarbonyl or ethoxycarbonyl, represents in each case optionally cyano-, fluorine-, chlorine-, methoxy-, ethoxy-, n- or i-propoxy-substituted acetyl, propionyl, n- or i-butyroyl, n- or i-propoxycarbonyl, methylaminocarbonyl, ethylaminocarbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, n- or i-butylaminocarbonyloxy, represents dimethylaminocarbonyl, diethylaminocarbonyl, dimethylaminocarbonyloxy or diethylaminocarbonyloxy, represents n- or i-butylcarbonyloxy, represents phenylcarbonyloxy, represents in each case optionally fluorine- or chlorine-substituted acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, or represents in each case optionally cyano-, carboxyl-, fluorine-, chlorine-, methoxycarbonyl- or ethoxycarbonyl-substituted ethenyl, propenyl, propenyloxy, propenyloxycarbonyl, ethinyl, propinyl, propinyloxy or propinyloxycarbonyl.

X most preferably represents in each case cyano-, carboxyl-, carbamoyl-, methoxy-, ethoxy-, n- or i-propoxy-, methoxycarbonyl-, ethoxycarbonyl-, n- or i-propoxycarbonyl-, allyloxycarbonyl-, 1-buten-3-yloxycarbonyl-, 2-buten-4-yloxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl- (and optionally additionally fluorine- or chlorine-) substituted methyl, ethyl, n-propyl, n-butyl, methoxy, ethoxy, n- or i-propoxy, n-, i- or s-butoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, diethylaminocarbonyloxy or phenylcarbonyloxy, represents n- or i-butylcarbonyloxy, represents dimethylamino, n- or i-butylaminocarbonyloxy, or represents in each case cyano-, carboxyl-, methoxycarbonyl- or ethoxycarbonyl- (and optionally additionally fluorine- or chlorine-) substituted ethenyl, propenyl, propenyloxy, ethinyl, propinyl or propinyloxy.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

A very particularly preferred group are the compounds of the formula (I)

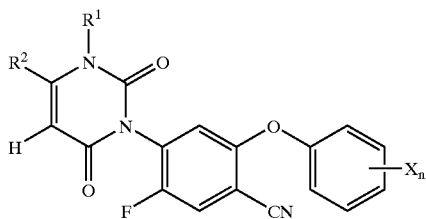

(I)

in which
n represents 1 or 2,
R¹ represents hydrogen or methyl,
R² represents trifluoromethyl, carbamoyl, carboxyl, methoxycarbonyl or cyano, and
X represents hydroxyl, mercapto, amino, nitro, cyano, carboxyl, carbamoyl, thiocarbamoyl, fluorine, chlorine, bromine, or represents in each case optionally cyano-, carboxyl-, carbamoyl-, fluorine-, chlorine-, methoxy-, ethoxy-, n- or i-propoxy-, methoxycarbonyl-, ethoxycarbonyl-, n- or i-propoxycarbonyl-, allyloxycarbonyl-, propargyloxycarbonyl-, 1-buten-3-yloxycarbonyl-, 2-buten-4-yloxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl- substituted methyl, ethyl, methoxy, ethoxy, methylthio, ethylthio, methoxycarbonyl or ethoxycarbonyl, or represents methoxycarbonyl- or ethoxycarbonyl-substituted ethenyl, or X represents in each case cyano-, carboxyl-, carbamoyl-, methoxy-, ethoxy-, n- or i-propoxy-, methoxycarbonyl-, ethoxycarbonyl-, n- or i-propoxycarbonyl-, allyloxycarbonyl-, 1-buten-3-yloxycarbonyl-, 2-buten-4-yloxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl- (and optionally additionally fluorine- or chlorine-) substituted methyl, ethyl, n-propyl, n-butyl, methoxy, ethoxy, n- or i-propoxy, n-, i- or s-butoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, diethylaminocarbonyloxy or phenylcarbonyloxy, represents n- or i-butylcarbonyloxy, represents dimethylamino, n- or i-butylaminocarbonyloxy, or represents in each case cyano-, carboxyl-, methoxycarbonyl- or ethoxycarbonyl- (and optionally additionally fluorine- or chlorine-) substituted ethenyl, propenyl, propenyloxy, ethinyl, propinyl or propinyloxy.

A further very particularly preferred group are those compounds of the formula (I) in which
n represents 1 or 2,
R¹ represents methyl,
R² represents trifluoromethyl, carbamoyl, carboxyl, cyano or methoxycarbonyl, and
X has one of the meanings given above for compounds of the formula (I).

A further very particularly preferred group are those compounds of the formula (I) in which
n represents 1 or 2,
R¹ represents hydrogen,
R² represents trifluoromethyl, carbamoyl, carboxyl, cyano or methoxycarbonyl, and
X has one of the meanings given above for compounds of the formula (I).

A further very particularly preferred group are those compounds of the formula (I) in which
n represents 1 or 2,
R¹ represents hydrogen or methyl,
R² represents trifluoromethyl, and
X has one of the meanings given above for compounds of the formula (I).

A further very particularly preferred group are those compounds of the formula (IA)

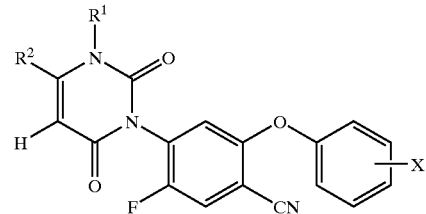

(IA)

in which
R¹ represents hydrogen or methyl,
R² represents trifluoromethyl, and
X represents in each case carboxyl-, methoxycarbonyl-, ethoxycarbonyl-, n- or i-propoxycarbonyl-, methylaminocarbonyl-, ethylaminocarbonyl-, dimethylaminocarbonyl-, diethylaminocarbonyl- or phenylaminocarbonyl-substituted methyl, ethyl, methoxy, ethoxy, or X represents n- or i-butylaminocarbonyloxy, n- or i-butylcarbonyloxy, dimethylamino, methoxycarbonyloxy, ethoxycarbonyloxy, methylaminocarbonyloxy, ethylaminocarbonyloxy, or represents dimethylaminocarbonyloxy.

A further very particularly preferred group are those compounds of the formula (IA) in which
R¹ represents hydrogen or methyl,
R² represents trifluoromethyl, and
X represents in each case carboxyl-, methoxycarbonyl- or ethoxycarbonyl-substituted methyl, methoxy or ethoxy, or
X represents methoxycarbonyloxy, ethoxycarbonyloxy, methylaminocarbonyloxy or ethylaminocarbonyloxy.

The abovementioned general or preferred radical definitions apply both to the end products of the formula (I) and, correspondingly, to the starting materials or intermediates required in each case for the preparation. These radical definitions can be combined with one another at will, i.e. including combinations between the given preferred ranges.

Examples of the compounds of the general formula (I) according to the invention are listed in the groups below.

Group 1

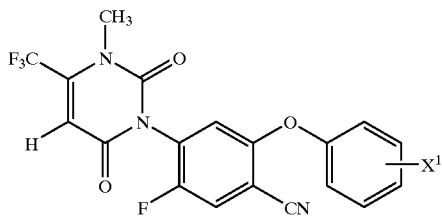

$X^1$ has here the meanings given in the list below:
4-(1-carboxy)-ethoxy, 4-(1-ethoxycarbonyl)-ethoxy, 3-(1-ethoxycarbonyl)-ethoxy, 3-ethoxycarbonylmethoxy, 2-(1-ethoxycarbonyl)-ethoxy.

Group 2

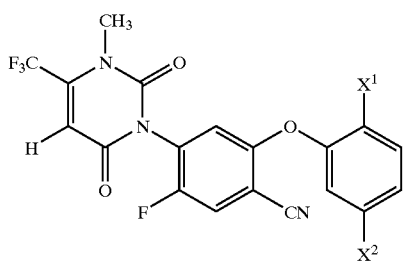

$X^1$ represents dimethylaminocarbonylmethoxy or methylaminocarbonylmethoxy and
$X^2$ represents methyl.

Group 3

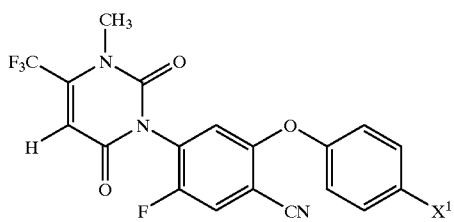

$X^1$ represents phenylaminocarbonylethoxy or phenylaminocarbonylmethoxy.

Group 4

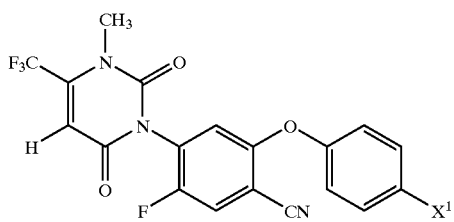

$X^1$ represents n- or i-butylcarbonyloxy or ethoxycarbonyloxy.

Group 5

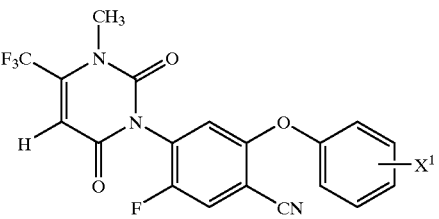

$X^1$ represents 4-ethylaminocarbonyloxy, 4-(n- or i-)butylaminocarbonyloxy, 3-methylaminocarbonyloxy or 2-methylaminocarbonyloxy.

Group 6

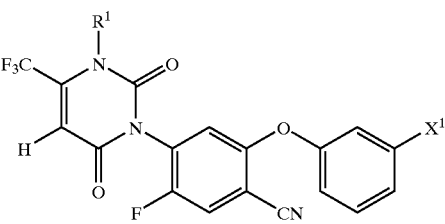

$X^1$ represents dimethylamino and
$R^1$ represents hydrogen or methyl.

Group 7

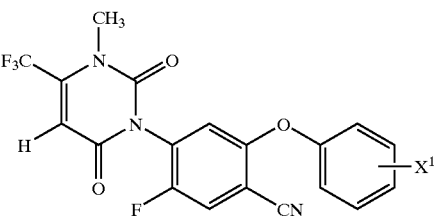

$X^1$ represents 2-chloro, 3-chloro, 4-chloro, 3-fluoro, 4-fluoro, 3-methyl, 3-cyano, 4-cyano, 2-methylthio, 2-methylsulphinyl or 4-methylsulphinyl.

Group 8

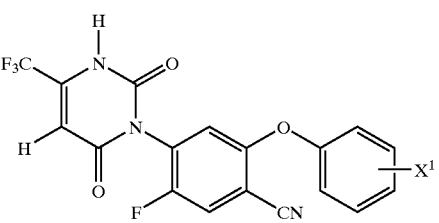

$X^1$ represents 2-chloro, 3-chloro, 4-chloro, 2-fluoro, 4-fluoro, 3-methyl, 3-nitro, 4-methyl, 3-cyano, 4-cyano, 2-methylthio, 4-nitro, 2-cyano, 4-methylthio or 2-methoxy.

Group 9

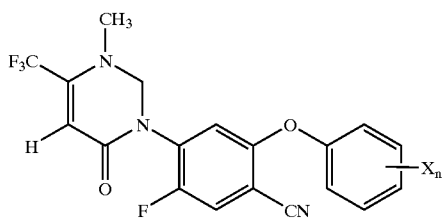

$X_n$ represents (3,4-)Cl$_2$ or (2,4-)F$_2$.

Group 10

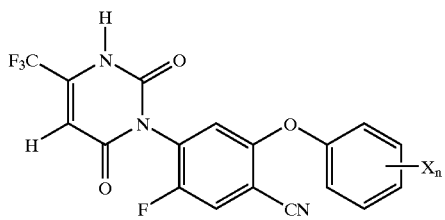

$X_n$ represents (3,4-)Cl$_2$ or (2,4-)F$_2$.

Group 11

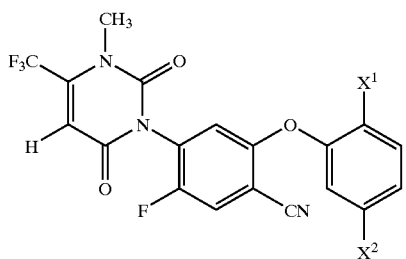

$X^1$ represents hydroxyl or methoxy, and
$X^2$ represents methyl.

Group 12

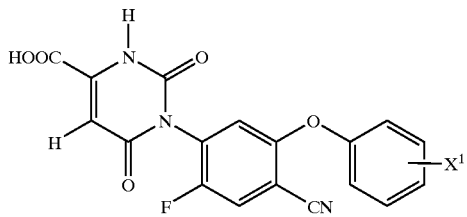

$X^1$ represents 4-methoxy, 3-chloro or 4-cyano.

Group 13

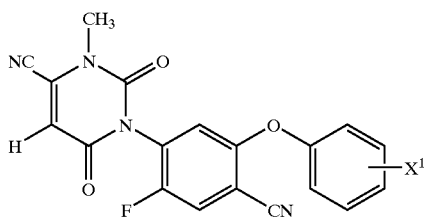

$X^1$ represents 3-trifluoromethyl, 4-chloro, 3-methoxy, 3-chloro or 4-cyano.

Group 14

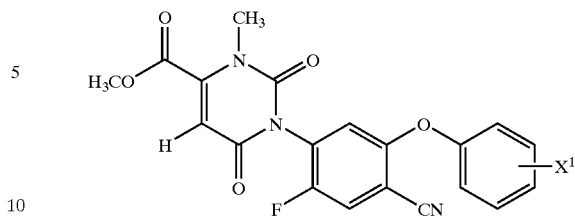

$X^1$ represents 3-methoxy, 3-chloro or 4-cyano.

Group 15

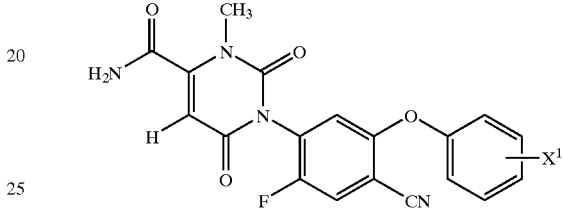

$X^1$ represents 3-trifluoromethyl, 4-chloro, 3-methoxy, 3-chloro or 4-cyano.

Group 16

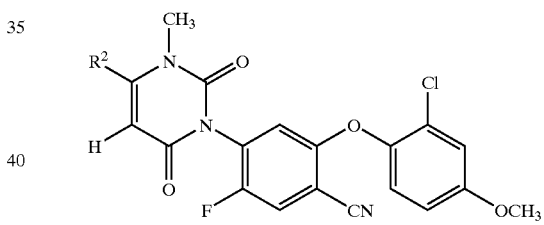

$R^2$ represents methoxycarbonyl, carbamoyl or cyano.

Group 17

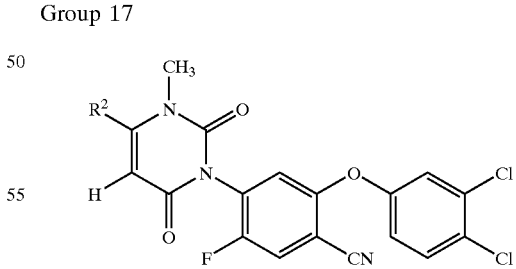

$R^2$ represents carbamoyl or cyano.

The novel substituted phenyluracils of the general formula (I) have interesting biological properties. In particular, they have strong herbicidal activity.

The novel substituted phenyluracils of the general formula (I) are obtained when (a) halogenophenyluracils of the general formula (II)

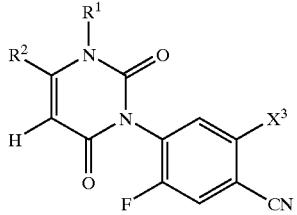
(II)

in which

R¹ and R² are each as defined above and

X³ represents halogen, are reacted with aryl compounds of the general formula (III)

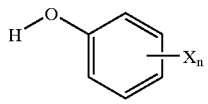
(III)

in which n and X are each as defined above, or with metal salts of compounds of the general formula (III), if appropriate in the presence of a reaction auxiliary and if appropriate in the presence of a diluent, or when (b) aminoalkenoic esters of the general formula (I)

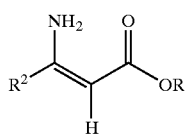
(IV)

in which

R² is as defined above and

R represents alkyl, aryl or arylalkyl, are reacted with aryl isocyanates of the general formula (V)

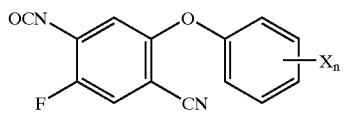
(V)

in which n and X are each as defined above, or with arylurethanes (arylcarbamates) of the general formula (VI)

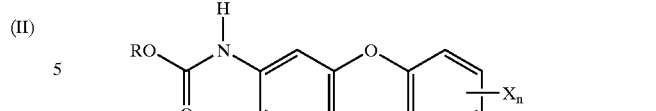
(VI)

in which n and X are each as defined above and

R represents alkyl, aryl or arylalkyl, if appropriate in the presence of a reaction auxiliary and if appropriate in the presence of a diluent, or when (c) N-aryl-1-alkoxycarbonylamino-maleimides of the general formula (VII)

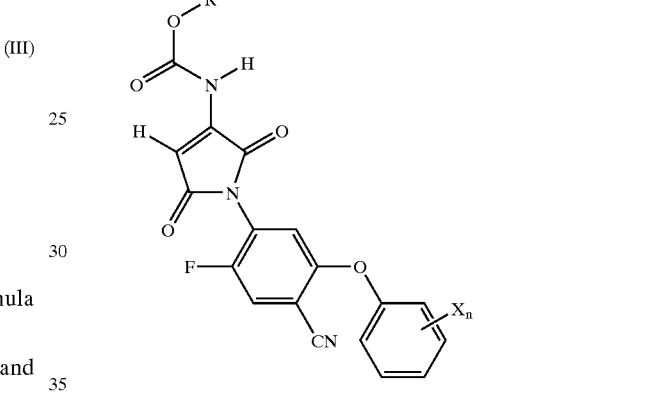
(VII)

in which n and X are each as defined above and

R' represents alkyl, are reacted with a metal hydroxide in the presence of water and, if appropriate, in the presence of an organic solvent, or when (d) substituted phenyluracils of the general formula (Ia)

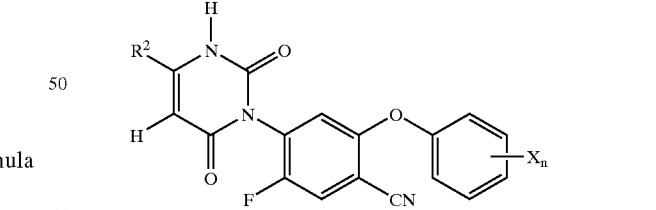
(Ia)

in which n and X are each as defined above are reacted with 1-aminooxy-2,4-dinitro-benzene or with alkylating agents of the general formula (VIII)

$$X^4 - A^1 \quad (VIII)$$

in which

A¹ represents optionally substituted alkyl and

X⁴ represents halogen or the grouping —O—SO₂—O—A¹, if appropriate in the presence of a reaction auxiliary and if appropriate in the presence of a diluent, and electrophilic or nucleophilic and/or oxidation or reduction reactions within the scope of the definition of the substituents are, if appropriate, subsequently carried out in a customary manner.

The compounds of the general formula (I) can be converted by customary methods into other compounds of the general formula (I) according to the above definition, for example by esterification or hydrolysis (for example X: $OCH_2COOH \rightarrow OCH_2COOC_2H_5$, $OCH(CH_3)COOCH_3 \rightarrow OCH(CH_3)COOH$), conversion of carboxyl compounds into other carboxylic acid derivatives by customary methods (for example $R^2$: $COOH \rightarrow CN$, $CN \rightarrow CSNH_2$, $COOH \rightarrow COOCH_3$, $COOCH_3 \rightarrow CONH_2$); cf. the Preparation Examples).

Using, for example, 1-(4-cyano-2,5-difluoro-phenyl)-4-chlorodifluoromethyl-3,6-dihydro-2,6-dioxo-1(2H)-pyrimidine and ethyl 1(4-hydroxy-phenoxy)-propionate as starting materials, the course of the reaction in the process (a) according to the invention can be illustrated by the following reaction scheme:

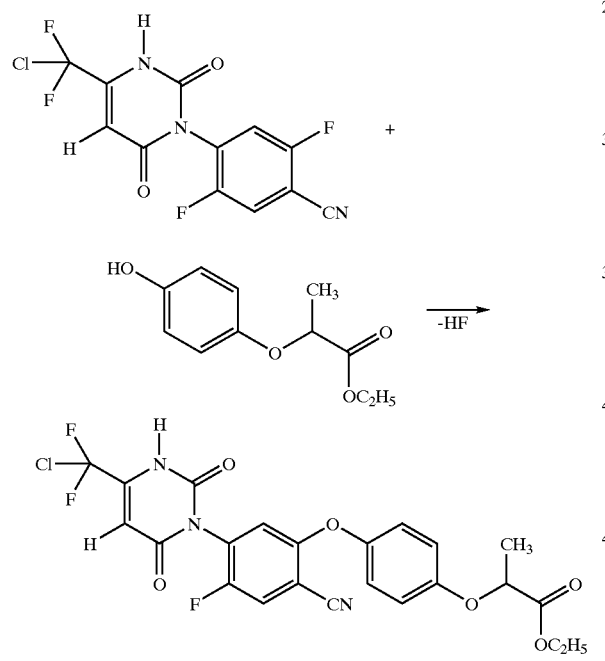

Using, for example, methyl 3-amino-4,4,4-trifluoro-crotonate and 4-cyano-2-fluoro-5-phenoxy-phenyl isocyanate as starting materials, the course of the reaction in process (b) according to the invention can be illustrated by the following reaction scheme:

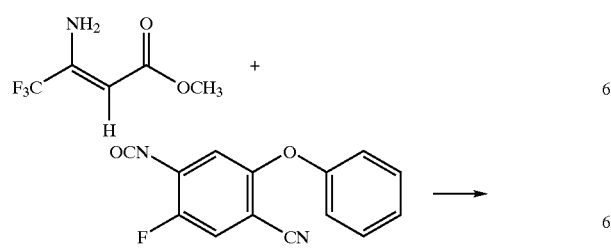

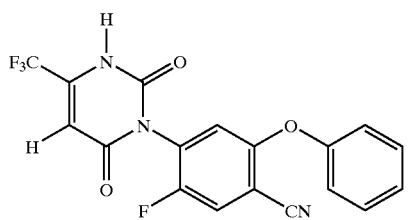

Using, for example, methyl [1-(4-cyano-2-fluoro-5-phenoxy-phenyl)-2,5-dioxo-2,5-dihydro-1H-pyrrol-3-yl]-carbamate as starting material, the course of the reaction in the process (c) according to the invention can be illustrated by the following reaction scheme:

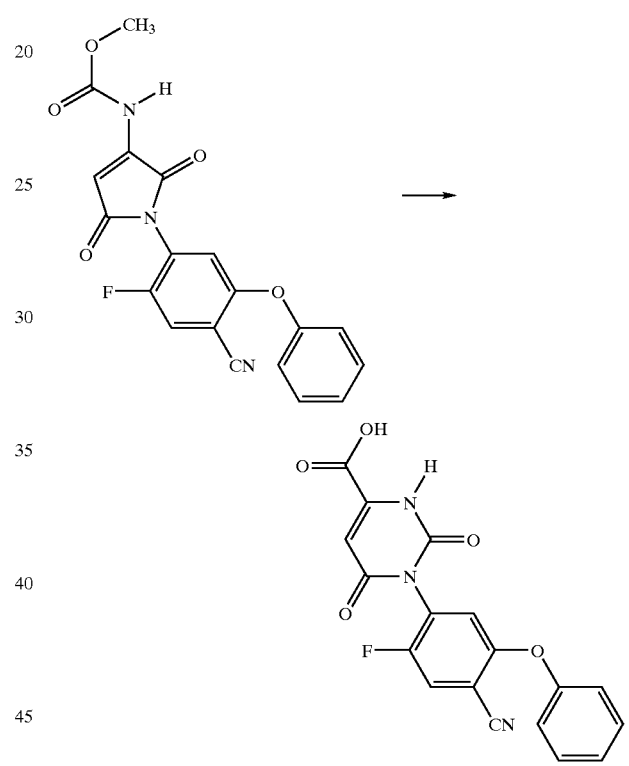

Using, for example, 1-[2-fluoro-4-cyano-5-(4-methoxycarbonylmethoxy-phenoxy)-phenyl]-4-difluoromethyl-3,6-dihydro-2,6-dioxo-1(2H)-pyrimidine and methyl bromide as starting materials, the course of the reaction in the process (d) according to the invention can be illustrated by the following reaction scheme:

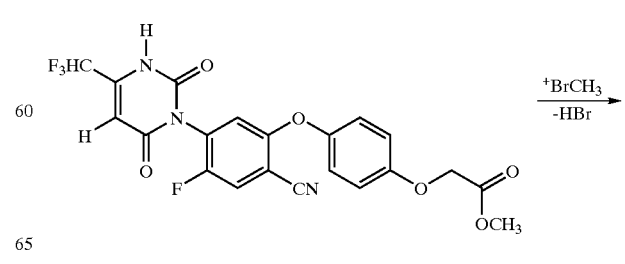

[Structure: pyrimidine-dione with CH3, F3HC, N, H, O substituents connected through phenyl-O-phenyl-O-CH2-C(=O)-OCH3 with F and CN groups]

The formula (II) provides a general definition of the halogenophenyluracils to be used as starting materials in the process (a) according to the invention for preparing compounds of the formula (I). In the formula (II), $R^1$ and $R^2$ each in particular have those meanings which have already been mentioned above, in connection with the description of the compounds of the formula (I) according to the invention, as being preferred, particularly preferred or very particularly preferred for $R^1$ and $R^2$; $X^3$ preferably represents fluorine or chlorine, in particular fluorine.

The starting materials of the general formula (II) are known and/or can be prepared by processes known per se (cf. EP-A-648749).

The formula (III) provides a general definition of the aryl compounds further to be used as starting materials in the process (a) according to the invention. In the formula (III), n and X each in particular have those meanings which have already been mentioned above, in connection with the description of the compounds of the formula (I) according to the invention, as being preferred, particularly preferred or very particularly preferred for n and X.

The starting materials of the general formula (III) are known organic chemicals for synthesis.

The formula (IV) provides a general definition of the aminoalkenoic esters to be used as starting materials in the process (b) according to the invention for preparing compounds of the general formula (I). In the general formula (IV), $R^2$ in particular has that meaning which has already been mentioned above, in connection with the description of the compounds of the general formula (I) according to the invention, as being preferred, particularly preferred or very particularly preferred for $R^2$; R preferably represents $C_1$–$C_4$-alkyl, phenyl or benzyl, in particular methyl or ethyl.

The starting materials of the general formula (IV) are known and/or can be prepared by processes known per se (cf. J. Heterocycl. Chem. 9 (1972), 513–522).

The formula (V) provides a general definition of the aryl isocyanates further to be used as starting materials in the process (b) according to the invention. In the general formula (V), n and X each in particular have those meanings which have already been mentioned above, in connection with the description of the compounds of the general formula (I) according to the invention, as being preferred, particularly preferred or very particularly preferred for n and X.

The novel aryl isocyanates of the general formula (V) are obtained when aniline derivatives of the general formula (IX)

[Structure IX: H2N and F on one phenyl ring with CN and O-linkage to another phenyl ring bearing $X_n$]

(IX)

in which n and X are each as defined above, are reacted with phosgene in the presence of a diluent, such as, for example, chlorobenzene, at temperatures between –20° C. and +150° C. (cf., for example, also EP-A-648749).

The formula (VI) provides a general definition of the arylurethanes to be used, if appropriate, as starting materials in the process (b) according to the invention. In the general formula (VI), n and X each in particular have those meanings which have already been mentioned above, in connection with the description of the compounds of the general formula (I) according to the invention, as being preferred, particularly preferred or very particularly preferred for n and X; R preferably represents $C_1$–$C_4$-alkyl, phenyl or benzyl, in particular methyl or ethyl.

The novel arylurethanes of the general formula (VI) are obtained when aniline derivatives of the general formula (IX)

[Structure IX: H2N and F on one phenyl ring with CN and O-linkage to another phenyl ring bearing $X_n$]

(IX)

in which n and X are each as defined above, are reacted with chlorocarbonyl compounds of the general formula (X)

$$RO\text{—}CO\text{—}Cl \quad (X)$$

in which

R is as defined above, if appropriate in the presence of an acid acceptor, such as, for example, pyridine, and if appropriate in the presence of a diluent, such as, for example, methylene chloride, at temperatures between –20° C. and +100° C. (cf. the Preparation Examples).

The aniline derivatives of the general formula (IX) required as precursors have hitherto not been disclosed.

The aniline derivatives of the general formula (IX)

[Structure IX: H2N and F on one phenyl ring with CN and O-linkage to another phenyl ring bearing $X_n$]

(IX)

in which n and X are each as defined above, are obtained when anilines of the general formula (XI)

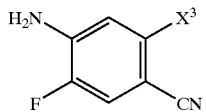
(XI)

in which

X³ is as defined above, are reacted with phenols of the general formula (III)

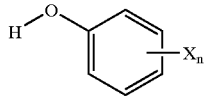
(III)

in which n and X are each as defined above, or with metal salts of compounds of the general formula (III), if appropriate in the presence of a reaction auxiliary, such as, for example, sodium hydride, and if appropriate in the presence of a diluent, such as, for example, N-methylpyrrolidone, at temperatures between 0° C. and 150° C. (cf. the Preparation Examples).

The formula (VII) provides a general definition of the N-aryl-1-alkoxycarbonyl-amino-maleimides to be used as starting materials in the process (c) according to the invention for preparing compounds of the general formula (I). In the general formula (VII), n and X each in particular have those meanings which have already been mentioned above, in connection with the description of the compounds of the general formula (I) according to the invention, as being preferred, particularly preferred or very particularly preferred for n and X; R' preferably represents $C_1$–$C_4$-alkyl, in particular methyl or ethyl.

The N-aryl-1-alkoxycarbonylamino-maleimides of the general formula (VII) are obtained when alkyl (2,5-dioxo-2,5-dihydro-furan-3-yl)-carbamates of the general formula (XII)

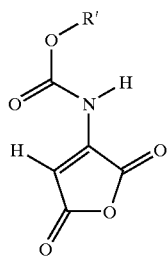
(XII)

in which

R' represents alkyl (in particular methyl or ethyl), are reacted with aniline derivatives of the general formula (IX)

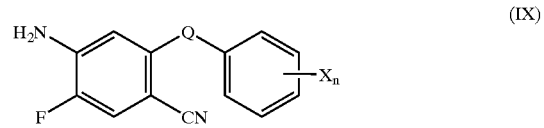
(IX)

in which n and X are each as defined above, if appropriate in the presence of a diluent such as, for example, acetic acid, at temperatures between 0° C. and 200° C., preferably between 50° C. and 150° C.

The precursors of the general formula (XII) are known and/or can be prepared by processes known per se (cf. DE 19604229).

The formula (Ia) provides a general definition of the substituted phenyluracils to be used as starting materials in the process (d) according to the invention for preparing compounds of the formula (I). In the formula (Ia), n and X each in particular have those meanings which have already been mentioned above, in connection with the description of the compounds of the formula (I) according to the invention, as being preferred, particularly preferred or very particularly preferred for n and X.

The starting materials of the general formula (Ia) for process (d) can be prepared by the processses (a), (b) and (c) according to the invention.

The formula (VIII) provides a general definition of the alkylating agents further to be used as starting materials in the process (d) according to the invention. In the formula (VIII), A¹ preferably represents optionally cyano-, halogen- or $C_1$–$C_4$-alkoxy-substituted alkyl having 1 to 4 carbon atoms and X² represents chlorine, bromine, iodine, methylsulphonyloxy or ethylsulphonyloxy: in particular, A¹ represents in each case optionally cyano-, fluorine-, chlorine-, methoxy- or ethoxy-substituted methyl, ethyl, n- or i-propyl and X² represents chlorine, bromine, iodine, methylsulphonyloxy or ethylsulphonyloxy.

The starting materials of the formula (VIII) are known organic chemicals for synthesis.

The processes according to the invention for preparing the compounds of the general formula (I) are preferably carried out using diluents. Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a), (b), (c) and (d) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane, (DABCO), 1,5-diazabicyclo[4.3.0]-non-5-ene (DBN) or 1,8-diazabicyclo[5.4.0]-undec-7-ene (DBU).

Suitable further reaction auxiliaries for the processses according to the invention are also phase-transfer catalysts. Examples of such catalysts which may be mentioned are:

Tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide, tetraphenylphosphonium bromide.

When carrying out the processes (a), (b), (c) and (d) according to the invention the reaction temperatures can be varied within a relatively wide range. In general, the processes are carried out at temperatures between 0° C. and 150° C., preferably between 10° C. and 120° C.

The processes according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used. The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium. However, the use of the active compounds according to the invention is in no way restricted to these genera, but also extends in the same manner to other plants. Depending on the concentration, the compounds are suitable for total weed control, for example on industrial terrain and rail tracks and on paths and areas with and without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on the soil and above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethacblor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethoflimesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulIfumn, iodosulfuron, ioxynil, isopropalin, isoproturon, isouron, isoxaben, isoxachlorbole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasuilfron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quimnerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuiron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

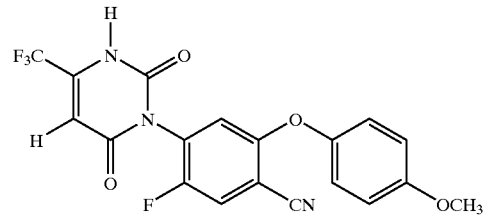

(Process (a))

2.5 g (10 mmol) of 4-methoxy-phenol are initially charged in 50 ml of dimethyl sulphoxide and admixed with 1.6 g of sodium hydride (60% pure). The mixture is stirred at room temperature (approximately 20° C.) for 30 minutes. 3.2 g (10 mmol) of 4-(3,6-dihydro-2,6-dioxo-4-trifluoromethyl-1(2H)-pyrimidin-1-yl)-2,5-difluoro-benzonitrile are then added. The reaction mixture is stirred at 60° C. for 18 hours and then poured into about the same amount by volume of 1N hydrochloric acid. The resulting crystalline product is isolated by filtration with suction, stirred with a mixture of 30 ml of ethyl acetate and 300 ml of diethyl ether and filtered off with suction until dry. The organic mother liquor is concentrated under waterpump vacuum and the residue is worked up by column chromatography (silica gel, chloroform/ethyl acetate, vol.: 2:1). The resulting first fraction is concentrated under waterpump vacuum, the residue is dissolved in boiling methylene chloride, the supernatant solvent is decanted off after cooling, the residue is stirred with diethyl ether/diisopropyl ether and the crystalline product is isolated by filtration with suction.

This gives 0.90 g (21% of theory) of 4-(3,6-dihydro-2,6-dioxo-4-trifluoromethyl-1(2H)-pyrimidin-1-yl)-5-fluoro-2-(4-methoxy-phenoxy)-benzonitrile of melting point 84° C.

Example 2

(Process (b))

A mixture of 0.50 g (1.2 mmol) of 4-(3,6-dihydro-2,6-dioxo-4-trifluoromethyl-1(2H)-pyrimidin-1-yl)-5-fluoro-2-(4-methoxy-phenoxy)-benzonitrile, 0.20 g (1.8 mmol) of dimethyl sulphate, 0.30 g (2.4 mmol) of potassium carbonate and 100 ml of acetone is heated under reflux for 15 hours and then concentrated under waterpump vacuum. The residue is shaken with 50 ml of 1N hydrochloric acid/50 ml of ethyl acetate and the organic phase is separated off, dried with sodium sulphate and filtered. The filtrate is concentrated under waterpump vacuum, dissolved in ethyl acetate, washed with 5% strength aqueous disodium hydrogen phosphate solution, dried with sodium sulphate and filtered. The filtrate is concentrated under waterpump vacuum, the residue is stirred with petroleum ether and the solvent is carefully distilled off under waterpump vacuum.

This gives 0.3 g (57% of theory) of 4-(3,6-dihydro-2,6-dioxo-3-methyl-4-trifluoro-methyl-1(2H)-pyrimidin-1-yl)-5-fluoro-2-(4-methoxy-phenoxy)-benzonitrile of melting point 62° C.

Analogously to Preparation Examples 1 and 2, and in accordance with the general description of the preparation processes according to the invention, it is also possible to prepare, for example, the compounds of the formula (I) listed in Table 1 below.

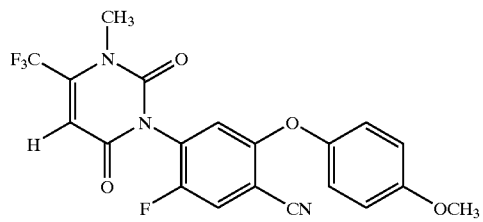

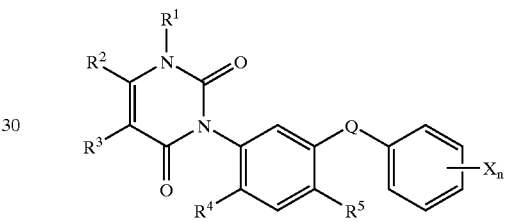

TABLE 1

Examples of the compounds of the formula (I)

| Ex. No. | N | Q | $R^1$ | $R^2$ | $R^3$ | $R^4$ | $R^5$ | (position-) X | Physical data and stereochem. specifications |
|---|---|---|---|---|---|---|---|---|---|
| 3 | 1 | O | $CH_3$ | $CF_3$ | H | F | CN | (4-) ⟶O–CH(CH$_3$)–COOC$_2$H$_5$ | racemate m.p.: 155° C. |
| 4 | 1 | O | $CH_3$ | $CF_3$ | H | F | CN | (4-) ⟶O–CH(CH$_3$)–COOH | racemate m.p.: 140° C. |
| 5 | 1 | O | $CH_3$ | $CF_3$ | H | F | CN | (4-) ⟶O–C(=O)–C(CH$_3$)$_3$ |  |
| 6 | 1 | O | $CH_3$ | $CF_3$ | H | F | CN | (4-) ⟶O–C(=O)–NH–C$_2$H$_5$ (O–methyl) | m.p.: 90° C. |

TABLE 1-continued

Examples of the compounds of the formula (I)

| Ex. No. | N | Q | R¹ | R² | R³ | R⁴ | R⁵ | (position-) X | | Physical data and stereochem. specifications |
|---|---|---|---|---|---|---|---|---|---|---|
| 7 | 1 | O | CH₃ | CF₃ | H | F | CN | (4-) | 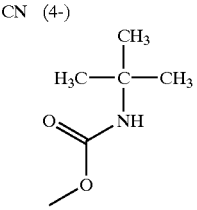 | m.p.: 110° C. |
| 8 | 1 | O | CH₃ | CF₃ | H | F | CN | (4-) | 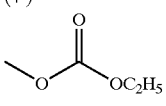 | |
| 9 | 1 | O | CH₃ | CF₃ | H | F | CN | (4-) | 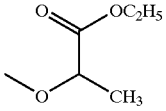 | (R isomer R/S = >9:<1) |
| 10 | 1 | O | CH₃ | CF₃ | H | F | CN | (4-) | 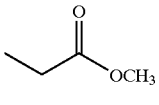 | m.p.: 152° C. δ = 6.55 ppm (s, D₆-DMSO) |
| 11 | 0 | O | H | CF₃ | H | F | CN | — | | m.p.: 223° C. |
| 12 | 0 | O | NH₂ | CF₃ | H | F | CN | — | | |
| 13 | 1 | O | CH₃ | CF₃ | H | F | CN | (2-)Cl | | m.p.: 206° C. |
| 14 | 1 | O | H | CF₃ | H | F | CN | (3-)Cl | | m.p.: 86° C. |
| 15 | 1 | O | CH₃ | CF₃ | H | F | CN | (3-)Cl | | m.p.: 101° C. |
| 16 | 1 | O | H | CF₃ | H | F | CN | (4-)Cl | | m.p.: 196° C. |
| 17 | 1 | O | CH₃ | CF₃ | H | F | CN | (4-)Cl | | m.p.: 150° C. |
| 18 | 1 | O | H | CF₃ | H | F | CN | (2-)F | | m.p.: 210° C. |
| 19 | 1 | O | CH₃ | CF₃ | H | F | CN | (3-)F | | m.p.: 78° C. |
| 20 | 1 | O | H | CF₃ | H | F | CN | (4-)F | | m.p.: 143° C. |
| 21 | 1 | O | CH₃ | CF₃ | H | F | CN | (4-)F | | m.p.: 169° C. |
| 22 | 2 | O | H | CF₃ | H | F | CN | (3,4-)Cl₂ | | δ = 6.43 ppm (s, D₆-DMSO) |
| 23 | 2 | O | CH₃ | CF₃ | H | F | CN | (3,4-)Cl₂ | | m.p.: 96° C. |
| 24 | 2 | O | H | CF₃ | H | F | CN | (2,4-)F₂ | | m.p.: 177° C. |
| 25 | 2 | O | CH₃ | CF₃ | H | F | CN | (2,4-)F₂ | | m.p.: 154° C. |
| 26 | 1 | O | H | CF₃ | H | F | CN | (3-)CH₃ | | m.p.: 139° C. logP = 2.92ᵃ⁾ |
| 27 | 1 | O | CH₃ | CF₃ | H | F | CN | (3-)CH₃ | | m.p.: 158° C. logP = 3.52ᵃ⁾ |
| 28 | 1 | O | H | CF₃ | H | F | CN | (3-)N(CH₃)₂ | | m.p.: 192° C. logp = 2.63ᵃ⁾ |
| 29 | 1 | O | CH₃ | CF₃ | H | F | CN | (3-) N(CH₃)₂ | | m.p.: 142° C. logP = 3.36ᵃ⁾ |
| 30 | 1 | O | H | CF₃ | H | F | CN | (3-)NO₂ | | m.p.: 183° C. |
| 31 | 1 | O | H | CF₃ | H | F | CN | (4-)CH₃ | | m.p.: 164° C. |
| 32 | 1 | O | H | CF₃ | H | F | CN | (3-)CN | | m.p.: 149° C. |
| 33 | 1 | O | CH₃ | CF₃ | H | F | CN | (3-)CN | | m.p.: 84° C. |
| 34 | 1 | O | H | CF₃ | H | F | CN | (4-)CN | | m.p.: 143° C. |
| 35 | 1 | O | CH₃ | CF₃ | H | F | CN | (4-)CN | | m.p.: 110° C. |
| 36 | 1 | O | H | CF₃ | H | F | CN | (2-)SCH₃ | | logP = 2.78ᵃ⁾ δ = 6.36 ppm (s, D₆-DMSO) |
| 37 | 1 | O | CH₃ | CF₃ | H | F | CN | (2-)SCH₃ | | m.p.: 120° C. logP = 3.36ᵃ⁾ |
| 38 | 1 | O | CH₃ | CF₃ | H | F | CN | (2-)SO₂CH₃ | | |
| 39 | 1 | O | H | CF₃ | H | F | CN | (2-)Cl | | |
| 40 | 1 | O | H | CF₃ | H | F | CN | (4-)NO₂ | | |
| 41 | 1 | O | H | CF₃ | H | F | CN | (2-)CN | | |
| 42 | 1 | O | H | CF₃ | H | F | CN | (4-)SCH₃ | | m.p.: 84° C. logP = 2.95ᵃ⁾ |

TABLE 1-continued

Examples of the compounds of the formula (I)

| Ex. No. | N | Q | R¹ | R² | R³ | R⁴ | R⁵ | (position-) X | Physical data and stereochem. specifications |
|---|---|---|---|---|---|---|---|---|---|
| 43 | 1 | O | CH₃ | CF₃ | H | F | CN | (4-)SO₂CH₃ | |
| 44 | 1 | O | CH₃ | CF₃ | H | F | CN | (3-) 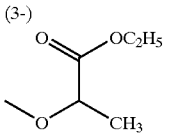 | R enantiomer δ = 6.56 ppm (s, D₆-DMSO) |
| 45 | 1 | O | CH₃ | CF₃ | H | F | CN | (3-) 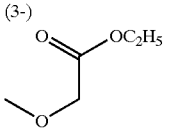 | δ = 6.56 ppm (s, D₆-DMSO) |
| 46 | 1 | O | CH₃ | CF₃ | H | F | CN | (3-) 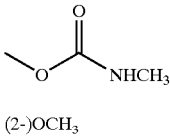 | δ = 6.56 ppm (s, D₆-DMSO) |
| 47 | 1 | O | H | CF₃ | H | F | CN | (2-)OCH₃ | m.p.: 86° C. |
| 48 | 1 | O | CH₃ | CF₃ | H | F | CN | (2-) 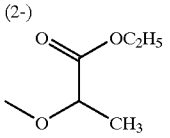 | |
| 49 | 1 | O | CH₃ | CF₃ | H | F | CN | (2-) 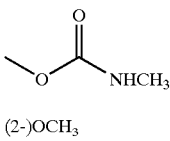 | m.p.: 108° C. log P = 2.66$^{a)}$ |
| 50 | 2 | O | CH₃ | CF₃ | H | F | CN | (2-)OCH₃ (5-)CH₃ | m.p.: 143° C. log P = 3.48$^{a)}$ |
| 51 | 2 | O | CH₃ | CF₃ | H | F | CN | (2-)OH (5-)CH₃ | m.p.: 174° C. log P = 2.96$^{a)}$ |
| 52 | 2 | O | CH₃ | CF₃ | H | F | CN | (2-) 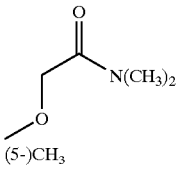 (5-)CH₃ | m.p.: 203° C. log P = 2.93$^{a)}$ |
| 53 | 2 | O | CH₃ | CF₃ | H | F | CN | (2-) 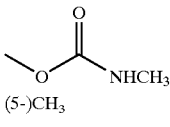 (5-)CH₃ | m.p.: 117° C. log P = 2.91$^{a)}$ |
| 54 | 2 | O | CH₃ | CF₃ | H | F | CN | (2-) 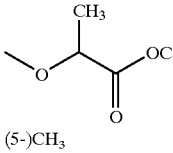 (5-)CH₃ | |
| 55 | 1 | O | CH₃ | CF₃ | H | F | CN | (4-) | m.p.: 91° C. |

TABLE 1-continued

Examples of the compounds of the formula (I)

| Ex. No. | N | Q | R¹ | R² | R³ | R⁴ | R⁵ | (position-) X | Physical data and stereochem. specifications |
|---|---|---|---|---|---|---|---|---|---|
| 56 | 1 | O | CH₃ | CF₃ | H | F | CN | (4-) 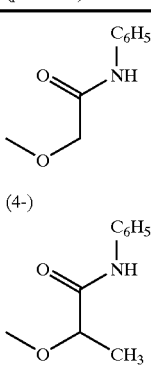 | m.p.: 97° C. (racemate) |
| 57 | 1 | O | H |  | H | F | CN | (4-)OCH₃ | |
| 58 | 2 | O | CH₃ |  | H | F | CN | (2-)Cl, (4-)OCH₃ | |
| 59 | 1 | O | CH₃ |  | H | F | CN | (3-)OCH₃ | |
| 60 | 1 | O | CH₃ |  | H | F | CN | (3-)CF₃ | logP = 2.40[a)] |
| 61 | 1 | O | CH₃ |  | H | F | CN | (4-)Cl | logP = 2.20[a)] |
| 62 | 2 | O | CH₃ |  | H | F | CN | (3-)Cl, (4-)Cl | logP = 2.51[a)] |
| 63 | 2 | O | CH₃ |  | H | F | CN | (2-)Cl, (4-)OCH3 | logP = 2.16[a)] |
| 64 | 1 | O | CH₃ |  | H | F | CN | (3-)OCH₃ | logP = 1.98[a)] |
| 65 | 1 | O | CH₃ | CN | H | F | CN | (3-)CF₃ | m.p.: 108° C. logP = 3.21[a)] |
| 66 | 1 | O | CH₃ | CN | H | F | CN | (4-)Cl | m.p.: 198° C. logP = 3.04[a)] |
| 67 | 1 | O | H |  | H | F | CN | (3-)Cl | logP = 1.89[a)] |
| 68 | 1 | O | H |  | H | F | CN | (4-)CN | logP = 1.49[a)] |

TABLE 1-continued

Examples of the compounds of the formula (I)

| Ex. No. | N | Q | R¹ | R² | R³ | R⁴ | R⁵ | (position-) X | Physical data and stereochem. specifications |
|---|---|---|---|---|---|---|---|---|---|
| 69 | 2 | O | CH₃ | CN | H | F | CN | (3-)Cl, (4-)Cl | m.p.: 191° C. logP = 3.37[a] |
| 70 | 1 | O | CH₃ | —CH(OCH₃)C(=O)— | H | F | CN | (3-)Cl | |
| 71 | 1 | O | CH₃ | —CH(OCH₃)C(=O)— | H | F | CN | (4-)CN | |
| 72 | 1 | O | CH₃ | —CH(NH₂)C(=O)— | H | F | CN | (3-)Cl | logP = 2.19[a] |
| 73 | 1 | O | CH₃ | —CH(NH₂)C(=O)— | H | F | CN | (4-)CN | logP = 1.75[a] |
| 74 | 2 | O | CH₃ | CN | H | F | CN | (2-)Cl, (4-)OCH3 | m.p.: 176° C. logP = 2.93[a] |
| 75 | 1 | O | CH₃ | CN | H | F | CN | (3-)OCH₃ | m.p.: 202° C. logP = 2.75[a] |
| 76 | 1 | 0 | CH₃ | CN | H | F | CN | (3-)Cl | m.p.: 80° C. logP = 3.04[a] |
| 77 | 1 | O | CH₃ | CN | H | F | CN | (4-)CN | m.p.: 232° C. logP = 2.44[a] |

The logP values given in Table 1 were determined in accordance with EEC directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding data in Table 1 are labelled a).

(b) Mobile phases for the determination in the neutral range: 0.01 molar aqueous phosphate buffer solution, acetonitrile; linear gradient from 10% acetonitrile to 90% acetonitrile—the corresponding data in Table 1 are labelled b).

Calibration was carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

Starting Materials of the Formula (VI):

Example (VI-1)

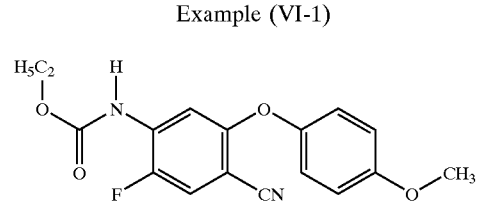

2.8 g (11 mmol) of 1-amino-4-cyano-2-fluoro-5-(4-methoxy-phenoxy)-benzene are initially charged in 100 ml of methylene chloride with 1.7 g of pyridine and, at room temperature (approximately 20° C.), admixed with 1.25 g (12 mmol) of ethyl chloroformate. The mixture is stirred at room temperature for 2 hours and then shaken with 1N hydrochloric acid. The organic phase is concentrated under waterpump vacuum, the residue is crystallized with diethyl ether/diisopropyl ether and the solid product is isolated by filtration with suction.

This gives 1.2 g (34% of theory) of O-ethyl N-(4-cyano-2-fluoro-5-(4-methoxy-phenoxy)-phenyl)-carbamate.
¹H-NMR (D6-DMSO, δ): 7.85 and 7.89 ppm.

Starting Materials of the Formula (IX):

Example (IX-1)

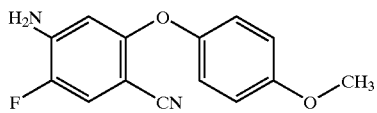

At room temperature, 1.3 g (10 mmol) of 4-methoxy-phenol in 100 ml of N-methyl-pyrrolidone are admixed with 0.50 g of sodium hydride (60% pure) and, after brief stirring, with 1.5 g of 4-cyano-2,5-difluoro-aniline. The reaction mixture is then stirred at 100° C. for 20 hours. After cooling, the mixture is diluted with water and then with 1N hydrochloric acid, and the mixture is stirred for two hours, after which the solid product is isolated by filtration with suction and dried on clay.

This gives 1.9 g (73% of theory) of 1-amino-4-cyano-2-fluoro-5-(4-methoxy-phenoxy)-benzene of melting point 135° C.

Analogously to Example (IX-1) it is also possible to prepare, for example, the compounds of the general formula (IX) listed in Table 2 below.

TABLE 2

Examples of the compounds of the formula (IX)

| Ex. No. | Q | $R^4$ | $R^5$ | $X_n$ | Physical data |
|---|---|---|---|---|---|
| IX-2 | O | F | CN | (3-)$OCH_3$ | m.p.: 94° C. |
| IX-3 | O | F | CN | (2-)$OCH_3$ | |
| IX-4 | O | F | CN | (4-)Cl | |
| IX-5 | O | F | CN | (3-)Cl | |
| IX-6 | O | F | CN | (2-)Cl | |
| IX-7 | O | F | CN | (4-)OH | |
| IX-8 | O | F | CN | (4-) 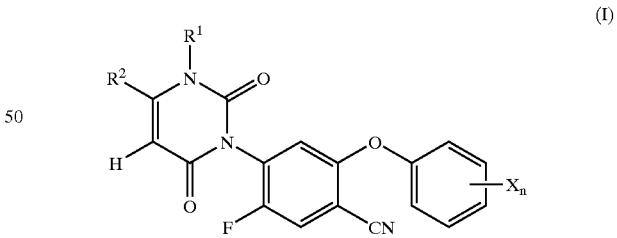 | |
| IX-9 | O | F | CN | — | |
| IX-10 | O | F | CN | (4-)F | |
| IX-11 | O | F | CN | (3-)F | |
| IX-12 | O | F | CN | (2-)F | |
| IX-13 | O | F | CN | (4-)Br | |
| IX-14 | O | H | CN | (4-)OH | |
| IX-15 | O | H | CN | (4-)$OCH_3$ | |
| IX-16 | O | H | CN | (4-)Cl | |
| IX-17 | O | H | CN | (4-)F | |
| IX-18 | O | F | $CF_3$ | — | |
| IX-19 | O | F | $CF_3$ | (4-)$CH_3$ | |
| IX-20 | O | F | $CF_3$ | (4-)$OCH_3$ | |
| IX-21 | S | H | CN | — | |
| IX-22 | S | F | CN | — | |
| IX-23 | S | F | CN | (4-)Cl | |
| IX-24 | S | F | CN | (4-)F | |
| IX-25 | O | F | $CF_3$ | (4-)CN | |

USE EXAMPLES

Example A

Pre-emergence Test

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liters of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Examples 4 and 6 show strong activity against weeds.

Example B

Post-emergence Test

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of preparation examples 4 and 6 show strong activity against weeds.

What is claimed is:

1. A phenyluracil of the Formula (I)

(I)

wherein n represents the numbers 0, 1 or 2, $R^1$ represents hydrogen, amino or optionally cyano-, carboxyl-, fluorine-, chlorine-, $C_1$–$C_4$-alkoxy- or $C_1$–$C_4$-alkoxy-carbonyl-substituted $C_1$–$C_4$-alkyl, $R^2$ represents carboxyl, cyano, carbamoyl, thiocarbamoyl or in each case optionally fluorine-substituted $C_1$–$C_4$-alkyl or $C_1$–$C_4$-alkoxy-carbonyl, X represents $C_1$–$C_4$-alkoxy-, $C_1$–$C_4$-alkylthio, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl-, $C_1$–$C_4$-alkenyloxycarbonyl-, $C_2$–$C_4$-alkinyl-oxycarbonyl-, $C_1$–$C_4$-alkylamino-carbonyl-, di-($C_1$–$C_4$-alkyl)-amino-carbonyl-, phenoxycarbonyl-, benzyloxycarbonyl-, phenylaminocarbonyl-substituted alkyl, alkoxy, alkylthio, alkylsulphinyl, alkylsulphonyl or alkylamino having in each case 1 to 6 carbon atoms, represents dialkylamino having in each case 1 to 6 carbon atoms in the alkyl groups, represents $C_1$–$C_4$-alkoxy-substituted alkylcarbonyl, alkoxycarbonyl, alkylaminocarbonyl, alkylcarbonyloxy, alkoxycarbonyloxy or alkylaminocarbonyloxy having in each case 1 to 6 carbon atoms in the alkyl groups, represents dialkylaminocarbonyl or dialkylaminocarbonyloxy having in each case 1 to 6 carbon atoms in the alkyl groups, represents phenylcarbonyloxy, represents in each case optionally fluorine-, chlorine- or bromine-substituted alkylcarbonylamino, alkoxycarbonylamino, alkylsulphonylamino, or represents in each case optionally cyano-, carboxyl-, fluorine-, chlorine-, bromine- or $C_1$–$C_4$-alkoxy-carbonyl-substituted alkenyl, alkenyloxy, alkenyloxy-carbonyl, alkinyl, alkinyloxy or alkinyloxycarbonyl having in each case up to 6 carbon atoms, where in the case that n is greater than 1, X may be the same or different.

2. A phenyluracil according to claim 1, wherein n represents the numbers 1 or 2, $R^1$ represents hydrogen, amino or optionally cyano-, carboxyl-, fluorine-, chlorine-, $C_1$–$C_4$-alkoxy- or $C_1$–$C_4$-alkoxy-carbonyl-substituted $C_1$–$C_4$-alkyl, $R^2$ represents carboxyl, cyano, carbamoyl, thiocarbamoyl or in each case optionally fluorine-substituted $C_1$–$C_4$-alkyl or $C_1$–$C_4$-alkoxy-carbonyl, and X represents hydroxyl, mercapto, amino, nitro, cyano, carboxyl, carbamoyl, thiocarbamoyl, fluorine, chlorine, bromine, iodine, represents in each case optionally hydroxyl-, cyano-, carboxyl-, carbamoyl-, fluorine-, chlorine-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkylcarbonyl-, $C_1$–$C_4$-alkoxy-carbonyl-, $C_2$–$C_4$-alkenyloxycarbonyl-, $C_2$–$C_4$-alkinyloxycarbonyl-, $C_1$–$C_4$-alkylamino-carbonyl-, di-($C_1$–$C_4$-alkyl)-amino-carbonyl-, phenoxycarbonyl-, benzyloxycarbonyl-, phenylamino-carbonyl-substituted alkyl, alkoxy, alkylthio, alkylsulphinyl, alkylsulphonyl or alkylamino having in each case 1 to 6 carbon atoms, represents dialkylamino having in each case 1 to 6 carbon atoms in the alkyl groups, represents in each case optionally cyano-, fluorine-, chlorine-, bromine- or $C_1$–$C_4$-alkoxy-substituted alkylcarbonyl, alkoxy-carbonyl, alkylaminocarbonyl, alkylcarbonyloxy, alkoxycarbonyloxy or alkylaminocarbonyloxy having in each case 1 to 6 carbon atoms in the alkyl groups, represents dialkylaminocarbonyl or dialkylaminocarbonyloxy having in each case 1 to 6 carbon atoms in the alkyl groups, represents phenylcarbonyloxy, represents in each case optionally fluorine-, chlorine- or bromine-substituted alkylcarbonylamino, alkoxycarbonylamino, alkylsulphonylamino, or represents in each case optionally cyano-, carboxyl-, fluorine-, chlorine-, bromine- or $C_1$–$C_4$-alkoxy-carbonyl-substituted alkenyl, alkenyloxy, alkenyloxy-carbonyl, alkinyl, alkinyloxy or alkinyloxycarbonyl having in each case up to 6 carbon atoms.

3. A phenyluracil according to claim 1, wherein n represents the number 1, $R^1$ represents hydrogen, amino or methyl, $R^2$ represents carboxyl, cyano, carbamoyl, methoxycarbonyl or trifluoromethyl, and X represents hydroxyl, mercapto, amino, nitro, cyano, carboxyl, carbamoyl, thiocarbamoyl, fluorine, chlorine, bromine, methyl, represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, allyloxy-carbonyl-, 1-buten-3-yloxycarbonyl-, 2-buten-4-yl-oxycarbonyl-, propargyloxycarbonyl-, 1-butin-3-yloxycarbonyl-, 2-butin-4-yloxycarbonyl-, methylaminocarbonyl-, ethylaminocarbonyl-, n- or i-propylaminocarbonyl, dimethylaminocarbonyl-, diethylamino-carbonyl-, phenoxycarbonyl-, benzyloxycarbonyl-, phenylaminocarbonyl- or benzylaminocarbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, methylsulphonyl, ethylsulphonyl, methylamino, ethylamino, n- or i-propylamino, n-, i-, s- or t-butylamino, represents dimethylamino or diethylamino, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or 1-propylaminocarbonyloxy, n- or i-butylaminocarbonyloxy, represents dimethylaminocarbonyl, diethylaminocarbonyl, dimethylaminocarbonyloxy or diethylaminocarbonyloxy, represents n- or i-butylcarbonyloxy, represents phenylcarbonyloxy, represents in each case optionally fluorine- or chlorine-substituted acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, or represents in each case optionally cyano-, carboxyl-, fluorine-, chlorine-, methoxycarbonyl- or ethoxycarbonyl-substituted ethenyl, propenyl, propenyloxy, propenyloxycarbonyl, ethinyl, propinyl, propinyloxy or propinyloxycarbonyl.

4. A phenyluracil according to claim 1, wherein

X represents hydroxyl, mercapto, amino, represents in each case cyano-, carboxyl-, carbamoyl-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxycarbonyl-, n-, i-, s- or t-butoxycarbonyl-, allyloxycarbonyl-, 1-buten-3-yloxycarbonyl-, 2-buten-4-yloxy-carbonyl-, propargyloxycarbonyl-, 1-butin-3-yloxycarbonyl-, 2-butin-4-yloxycarbonyl-, methylamino-carbonyl-, ethylaminocarbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted methyl, methoxy, ethyl, n- or i-propyl, n-, i-, s- or t-butyl, ethoxy, n- or i-propoxy, methylthio, ethylthio, methylsulphinyl, ethylsulphinyl, methylsulphonyl or ethylsulphonyl, represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, n- or i-butyroyl-, methoxycarbonyl-, ethoxycarbonyl-, n- or i-propoxy-carbonyl-, allyloxycarbonyl-, 1-buten-3-yloxycarbonyl-, 2-buten-4-yl-oxycarbonyl-, propargyloxycarbonyl-, 1-butin-3-yloxy-carbonyl-, 2-butin-4-yloxycarbonyl-, methylaminocarbonyl-, ethylamino-carbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl-substituted n-, i-, s- or t-butoxy, n- or i-propylthio, methylamino, ethylamino, n- or i-propylamino, n-, i-, s- or t-butylamino, represents dimethylamino or diethylamino, represents in each case cyano-, fluorine-, chlorine-, methoxy-, ethoxy-, n- or i-propoxy-substituted methoxycarbonyl or ethoxycarbonyl, represents in each case optionally cyano-, fluorine-, chlorine-, methoxy-, ethoxy-, n- or i-propoxy-substituted acetyl, propionyl, n- or i-butyroyl, n- or i-propoxycarbonyl, methoxycarbonyl, ethylamino-carbonyl, n- or i-propylaminocarbonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, n- or i-butylaminocarbonyloxy, represents dimethylaminocarbonyl, diethylaminocarbonyl, dimethylaminocarbonyloxy or diethylaminocarbonyloxy, represents n- or i-butylcarbonyloxy, represents phenylcarbonyloxy, represents in each case optionally fluorine- or chlorine-substituted acetylamino, propionylamino, n- or i-butyroylamino, methoxycarbonylamino, ethoxycarbonylamino, n- or i-propoxycarbonylamino, methylsulphonylamino, ethylsulphonylamino, n- or i-propylsulphonylamino, n-, i-, s- or t-butylsulphonylamino, or represents in each case optionally cyano-, carboxyl-, fluorine-, chlorine-, methoxycarbonyl- or ethoxycarbonyl-substituted ethenyl, propenyl, propenyloxy, propenyloxycarbonyl, ethinyl, propinyl, propinyloxy or propinyloxycarbonyl.

5. A phenyluracil according to claim 1, wherein

X represents in each case cyano-, carboxyl-, carbamoyl-, methoxy-, ethoxy-, n- or i-propoxy-, methoxycarbonyl-, ethoxycarbonyl-, n- or i-propoxycarbonyl-, allyloxycarbonyl-, 1-buten-3-yloxycarbonyl-, 2-buten-4-yloxycarbonyl-, propargyloxycarbonyl-, 1-butin-3-yloxy-carbonyl-, 2-butin-4-yloxycarbonyl-, methylaminocarbonyl-, ethylamino-carbonyl-, n- or i-propylaminocarbonyl, dimethylaminocarbonyl-, diethylaminocarbonyl-, phenoxycarbonyl-, benzyloxycarbonyl-, phenylaminocarbonyl- or benzylaminocarbonyl- (and optionally additionally fluorine- or chlorine-) substituted methyl, ethyl, n-propyl, n-butyl, methoxy, ethoxy, n- or i-propoxy, n-, i- or s-butoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, diethylaminocarbonyloxy or phenylcarbonyloxy, represents n- or i-butylcarbonyloxy, represents dimethylamino, n- or i-butylaminocarbonyloxy, or represents in each case cyano-, carboxyl-, methoxycarbonyl- or ethoxycarbonyl- (and optionally additionally fluorine- or chlorine-) substituted ethenyl, propenyl, propenyloxy, ethinyl, propinyl or propinyloxy.

6. A phenyluracil according to claim 1, wherein n represents 1 or 2, $R^1$ represents hydrogen or methyl, $R^2$ represents trifluoromethyl, carbamoyl, carboxyl, methoxycarbonyl or cyano, and X represents hydroxyl, mercapto, amino, nitro, cyano, carboxyl, carbamoyl, thiocarbamoyl, fluorine, chlorine, bromine, or represents in each case optionally cyano-, carboxyl-, carbamoyl-, fluorine-, chlorine-, methoxy-, ethoxy-, n- or i-propoxy-, methoxycarbonyl-, ethoxycarbonyl-, n- or i-propoxycarbonyl-, allyloxycarbonyl-, propargyloxycarbonyl-, 1-buten-3-yloxycarbonyl-, 2-buten-4-yloxy-carbonyl-, propargyloxy-carbonyl-, 1-butin-3-yloxycarbonyl-, 2-butin-4-yloxycarbonyl-, methylaminocarbonyl-, ethylaminocarbonyl-, n- or i-propylaminocarbonyl-, dimethylaminocarbonyl, diethylamino-carbonyl-, phenoxycarbonyl-, benzyloxycarbonyl-, phenylaminocarbonyl- or benzylaminocarbonyl-substituted methyl, ethyl, methoxy, ethoxy, methylthio, ethylthio, methoxycarbonyl or ethoxycarbonyl, or represents methoxycarbonyl- or ethoxycarbonyl-substituted ethenyl, or X represents in each case cyano-, carboxyl-, carbamoyl-, methoxy-, ethoxy-, n- or i-propoxy-, methoxycarbonyl-, ethoxycarbonyl-, n- or i-propoxycarbonyl-, allyloxycarbonyl-, 1-buten-3-yl-oxycarbonyl-, 2-buten-4-yloxycarbonyl-, propargyloxycarbonyl-, 1-butin-3-yloxy-carbonyl -, 2-butin-4-yloxycarbonyl-, methylaminocarbonyl-, ethylamino-carbonyl-, n- or i-propylaminocarbonyl-, dimethylaminocarbonyl-, diethylaminocarbonyl-, phenoxycarbonyl-, benzyloxycarbonyl-, phenylaminocarbonyl- or benzylaminocarbonyl- (and optionally additionally fluorine- or chlorine-) substituted methyl, ethyl, n-propyl, n-butyl, methoxy, ethoxy, n- or i-propoxy, n-, i- or s-butoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, diethylaminocarbonyloxy or phenylcarbonyloxy, represents n- or i-butylcarbonyloxy, represents dimethylamino, n- or i-butylaminocarbonyloxy, or represents in each case cyano-, carboxyl-, methoxycarbonyl- or ethoxycarbonyl- (and optionally additionally fluorine- or chlorine-) substituted ethenyl, propenyl, propenyloxy, ethinyl, propinyl or propinyloxy.

7. A phenyluracil according to claim 1, wherein n represents 1 or 2, $R^1$ represents methyl, $R^2$ represents trifluoromethyl, carbamoyl, carboxyl, cyano or methoxycarbonyl.

8. A phenyluracil according to claim 1, wherein n represents 1 or 2, $R^1$ represents hydrogen, and $R^2$ represents trifluoromethyl, carbamoyl, carboxyl, cyano or methoxycarbonyl.

9. A substituted phenyluracil according to claim 1, wherein n represents 1 or 2, $R^1$ represents hydrogen or methyl, and $R^2$ represents trifluoromethyl.

10. A compound of the Formula (IA)

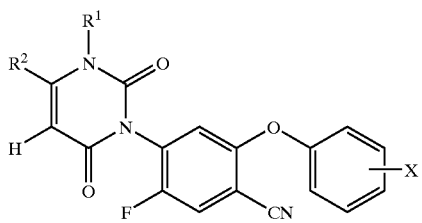

(IA)

wherein $R^1$ represents hydrogen or methyl, $R^2$ represents trifluoromethyl, and X represents in each case carboxyl-, methoxycarbonyl-, ethoxycarbonyl-, n- or i-propoxycarbonyl-, methylaminocarbonyl-, ethylaminocarbonyl-, dimethylaminocarbonyl-, diethylaminocarbonyl- or phenylaminocarbonyl-substituted methyl, ethyl, methoxy, ethoxy, or X represents n- or i-butylaminocarbonyloxy, n- or i-butylcarbonyloxy, dimethylamino, methoxycarbonyloxy, ethoxycarbonyloxy, methylaminocarbonyloxy, ethylaminocarbonyloxy, or represents dimethylaminocarbonyloxy.

11. A compound of the Formula (IA) according to claim 10, wherein $R^1$ represents hydrogen or methyl, $R^2$ represents trifluoromethyl, and X represents in each case carboxyl-, methoxycarbonyl- or ethoxy-carbonyl-substituted methyl, methoxy or ethoxy, or X represents methoxycarbonyloxy, ethoxycarbonyloxy, methylaminocarbonyloxy or ethylaminocarbonyloxy.

12. A compound of the Formula (IB)

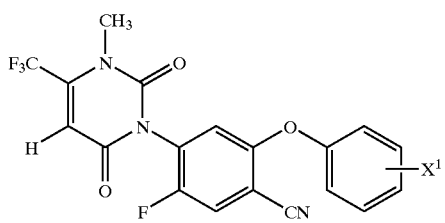

(IB)

wherein $X^1$ represents 4-(1-carboxy)-ethoxy, 4-(1-ethoxycarbonyl)-ethoxy, 3-(1-ethoxycarbonyl)-ethoxy, 3-ethoxycarbonylmethoxy or 2-(1-ethoxy-carbonyl)-ethoxy.

13. A compound of the Formula (IB) according to claim 12, wherein $X^1$ represents 4-ethylaminocarbonyloxy, 4-(n- or i-)butylaminocarbonyloxy, 3-methylaminocarbonyloxy or 2-methylaminocarbonyloxy.

14. A compound of the Formula (IB) according to claim 12, wherein $X^1$ represents 2-chloro, 3-chloro, 4-chloro, 3-fluoro, 4-fluoro, 3-methyl, 3-cyano, 4-cyano, 2-methylthio, 2-methylsulphinyl or 4-methylsulphinyl.

15. A compound of the Formula (IC)

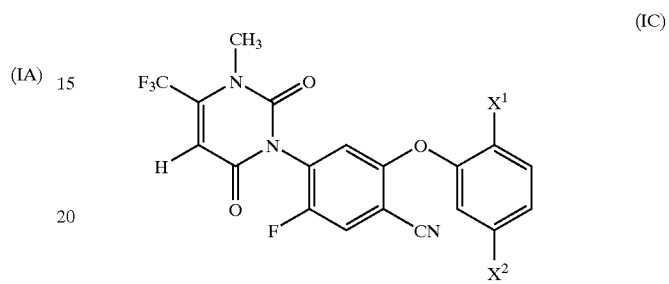

(IC)

wherein $X^1$ represents dimethylaminocarbonylmethoxy or methylaminocarbonylmethoxy and $X^2$ represents methyl.

16. A compound of the Formula (IC) according to claim 15, wherein $X^1$ represents hydroxyl or methoxy, and $X^2$ represents methyl.

17. A compound of the Formula (ID)

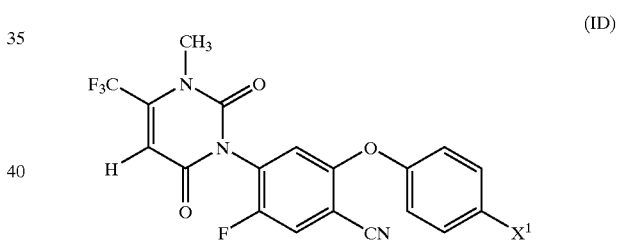

(ID)

wherein $X^1$ represents phenylaminocarbonylethoxy or phenylaminocarbonylmethoxy.

18. A compound of the Formula (ID) according to claim 17, wherein $X^1$ represents n- or i-butylcarbonyloxy or ethoxycarbonyloxy.

19. A compound of the Formula (IE)

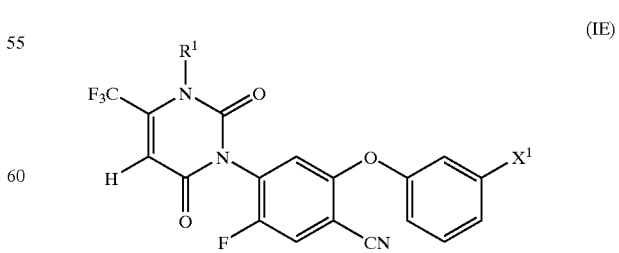

(IE)

wherein $X^1$ represents dimethylamino and $R^1$ represents hydrogen or methyl.

20. A compound of the Formula (IF)

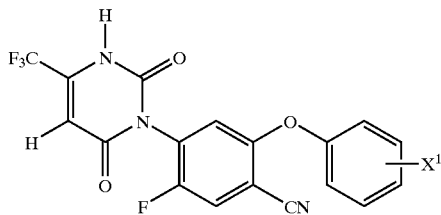
(IF)

wherein

X¹ represents 2-chloro, 3-chloro, 4-chloro, 2-fluoro, 4-fluoro, 3-methyl, 3-nitro, 4-methyl, 3-cyano, 4-cyano, 2-methylthio, 4-nitro, 2-cyano, 4-methylthio or 2-methoxy.

21. A compound of the Formula (IG)

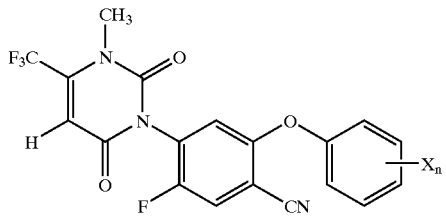
(IG)

wherein $X_n$ represents (3,4-)Cl$_2$ or (2,4-)F$_2$.

22. A compound of the Formula (IH)

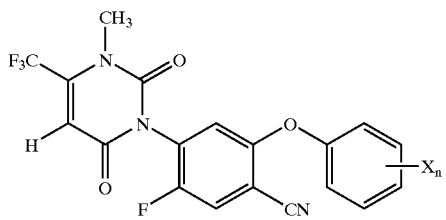
(IH)

wherein $X_n$ represents (3,4-)Cl$_2$ or (2,4-)F$_2$.

23. A compound of the Formula (IJ)

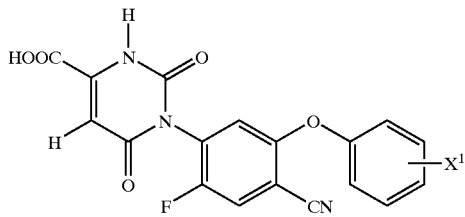
(IJ)

wherein

X¹ represents 4-methoxy, 3-chloro or 4-cyano.

24. A compound of the Formula (IK)

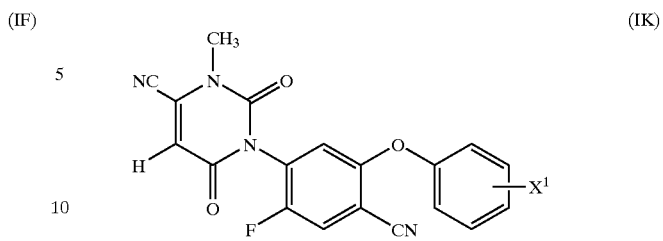
(IK)

wherein

X¹ represents 3-trifluoromethyl, 4-chloro, 3-methoxy, 3-chloro or 4-cyano.

25. A compound of the Formula (IL)

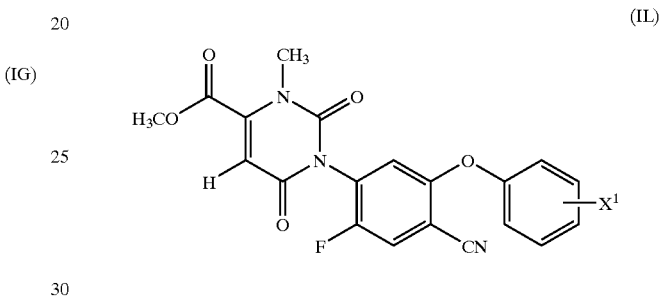
(IL)

wherein

X¹ represents 3-methoxy, 3-chloro or 4-cyano.

26. A compound of the Formula (IM)

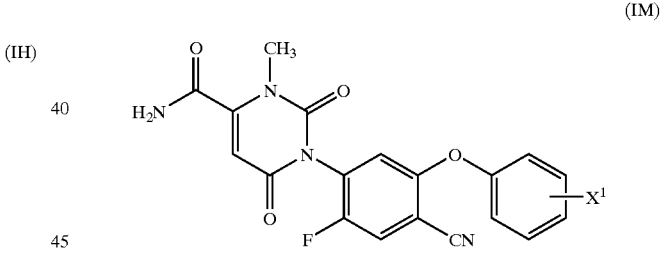
(IM)

wherein

X¹ represents 3-trifluoromethyl, 4-chloro, 3-methoxy, 3-chloro or 4-cyano.

27. A compound of the Formula (IN)

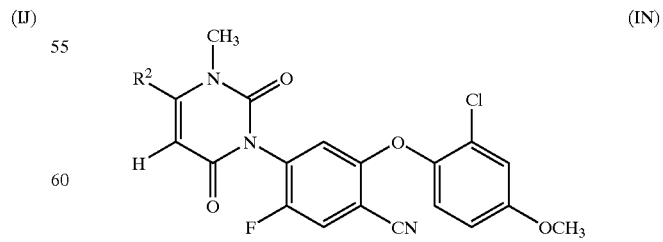
(IN)

wherein

R² represents methoxycarbonyl, carbamoyl or cyano.

28. A compound of the Formula (IO)

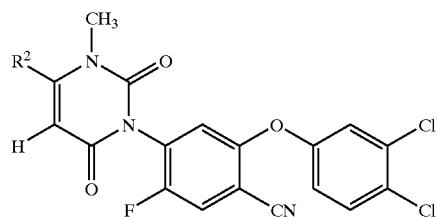

wherein

R² represents carbamoyl or cyano.

29. An herbicidal composition comprising one or more substituted phenyluracil according to claim 1 and one or more extenders.

30. A method for controlling undesirable plants comprising the step of applying an effective amount of one or more substituted phenyluracils according to claim 1 to a member selected from the group consisting of said plant, a habitat of said plant and combinations thereof.

* * * * *